United States Patent
Takahashi et al.

(10) Patent No.: US 7,915,051 B2
(45) Date of Patent: Mar. 29, 2011

(54) BIOSENSOR AND BLOOD COMPONENT ANALYTICAL METHOD

(75) Inventors: Mie Takahashi, Ehime (JP); Masataka Nadaoka, Ehime (JP); Hirotaka Tanaka, Ehime (JP); Fumihisa Kitawaki, Osaka (JP)

(73) Assignee: Panasonic Corporation, Osaka (JP)

( * ) Notice: Subject to any disclaimer, the term of this patent is extended or adjusted under 35 U.S.C. 154(b) by 470 days.

(21) Appl. No.: 11/950,671

(22) Filed: Dec. 5, 2007

(65) Prior Publication Data

US 2008/0083619 A1 Apr. 10, 2008

Related U.S. Application Data

(62) Division of application No. 10/049,366, filed as application No. PCT/JP01/04649 on Jun. 1, 2001.

(30) Foreign Application Priority Data

Jun. 1, 2000 (JP) .................................. 2000-164990

(51) Int. Cl.
   *G01N 33/53* (2006.01)
(52) U.S. Cl. .................. 436/517; 435/287.1; 435/287.9; 436/514; 436/518
(58) Field of Classification Search ............... 435/287.1, 435/287.9; 436/514, 518, 517
   See application file for complete search history.

(56) References Cited

U.S. PATENT DOCUMENTS

| | | | |
|---|---|---|---|
| 3,552,928 A * | 1/1971 | Fetter | 422/56 |
| 4,186,224 A | 1/1980 | Grillo | |
| 4,259,207 A | 3/1981 | Fruitstone et al. | |
| 4,477,575 A | 10/1984 | Vogel et al. | |
| 4,816,224 A | 3/1989 | Vogel et al. | |
| 4,978,624 A | 12/1990 | Cremins et al. | |
| 5,166,051 A | 11/1992 | Killeen et al. | |
| 5,350,693 A | 9/1994 | Maimon et al. | |
| 5,607,863 A | 3/1997 | Chandler | |
| 5,755,231 A | 5/1998 | Krantz et al. | |
| 5,939,331 A | 8/1999 | Burd et al. | |
| 6,197,598 B1 | 3/2001 | Schrier et al. | |
| 6,352,862 B1 | 3/2002 | Davis et al. | |
| 6,358,752 B1 | 3/2002 | Durst et al. | |

FOREIGN PATENT DOCUMENTS

| | | |
|---|---|---|
| EP | 0214613 | 3/1987 |
| EP | 0903584 | 3/1999 |
| EP | 1143247 | 10/2001 |
| EP | 1202059 | 5/2002 |
| JP | 5753661 | 3/1982 |
| JP | 01262470 | 10/1989 |
| JP | 06094718 | 4/1994 |
| JP | 09072904 | 3/1997 |
| JP | 09196908 | 7/1997 |
| JP | 11505327 | 5/1999 |
| SU | 1140462 | 5/1986 |
| WO | WO-9635952 | 11/1996 |

* cited by examiner

*Primary Examiner* — Bao-Thuy L Nguyen
(74) *Attorney, Agent, or Firm* — Marjama Muldoon Blasiak & Sullivan LLP (57) ABSTRACT

According to the biosensor and the blood component analytical method of the present invention, in a biosensor that is made of a single layer or plural layers of a porous material as shown in FIG. 1, having a reagent holding part and utilizing chromatography, a cell shrinkage reagent is carried on at least part of the reagent holding part, or at least part of a chromatographically developed part that is upstream of the reagent holding part. According to the biosensor having the above-mentioned structure and the blood component analytical method, even when whole blood is a sample, a high-accuracy blood component analysis cart be performed easily and quickly with less cost.

1 Claim, 6 Drawing Sheets

BIOSENSOR AND BLOOD COMPONENT ANALYTICAL METHOD

CROSS REFERENCE TO RELATED APPLICATIONS

This application is a divisional of U.S. Ser. No. 10/049,366, filed May 10, 2002, which is a national stage application of PCT/JP01/04649 filed Jun. 1, 2001, which claims priority from JP2000-164990, filed Jun. 1, 2000 which these applications are incorporated herein by reference.

TECHNICAL FIELD

The present invention relates to a biosensor for analyzing blood components and a blood component analytical method and, more particularly, to a biosensor that is less affected by cell components such as hemocytes, as well as enables simple and quick measurement with high accuracy using a very small quantity of samples, and a blood component analytical method.

BACKGROUND ART

Biochemical tests for blood are widely carried out as means for diagnosing the conditions of human's health. It is difficult to measure the kinds or concentrations of constitutive components in blood, such as metabolites, proteins, lipids, electrolytes, enzymes, antigens and antibodies, using whole blood, and thus they are normally measured using plasma or serum which is obtained by centrifuging whole blood as a sample.

The centrifugation requires times and efforts, and a centrifugation method requiring a centrifuge is unsuitable for cases where a particularly small quantity of samples are to be processed urgently or for on-site tests. Further, the quantity of serum or plasma obtained by the centrifugation is smaller than the quantity of blood which has been obtained by blood collection.

Thus, as blood component analytical methods which are not affected by cell components such as hemocytes even when whole blood is used as a sample, blood component analytical methods such as those disclosed in Japanese Published Patent Applications No. Sho 57-53661 and No. Hei. 8-54387, employing a hemocyte separation method by which blood is exuded using glass fiber filter paper having an average diameter of. 0.2-5 μm and a density of 0.1-0.5 g/cm$^3$ thereby separating plasma or serum, or a blood component analytical method such as one disclosed in Japanese Published Patent Application No. Hei. 9-196908, employing a blood regulation method by which an aqueous solution of amino acid or inorganic salt is mixed with whole blood and thereafter hemocyte components are filtered, thereby avoiding clogging of filtered materials due to hemocytes, and a larger quantity of plasma or serum components are obtained using a smaller quantity of blood have been examined.

Further, a method as disclosed in Japanese Published Patent Application No. Hei. 9-72904, by which blood is hemolyzed by a surfactant carried on a test strip and then a sample solution is developed on the test strip using a development solution has been examined.

It is true that the method employing the glass fiber filter paper of the prescribed density improves the hemocyte separation efficiency, but it takes quite a long time to separate hemocytes almost completely. Thus, the measurement cannot be performed quickly, and further not only a large quantity of blood is required to obtain a quantity of samples that is necessary for the test, but also the blood viscosities or hematocrit values differ among individuals so that the separation power has individual differences and thus the measurement accuracy is quite low. Further, it requires special filter paper, thereby being costly.

In the method by which an aqueous solution of the prescribed concentration of mineral salt or amino acid is added to whole blood and then hemocyte components are filtered, the efforts for hemocyte separation by the centrifugation are omitted, but the operation of previously adding an additive liquid to the blood to be processed is so complicated that it lack the simplicity as well as the measurement takes much time.

Further, in the method of previously hemolyzing blood, the basic principle of hemolysis is destroying a bilayer lipid membrane in the cell membrane of the hemocyte using a surfactant or a hemolyzer such as saponin, and crushing a hemocyte cell to pieces. In the case of a very small quantity of blood, the development solution is added after the hemolysis is performed, thereby enabling development on a chromatographic device. However, when the development solution is not used, the development layer is clogged with cell pieces, so that the collected blood sample cannot be developed without the development solution.

The present invention is made to solve the above-mentioned problems and has for its object to provide a one-step biosensor and a blood component analytical method, which can perform a high-accuracy blood component analytical method easily and quickly, with less expenses and without the need to previously carry out any processing for blood or the need for a development solution for developing a sample solution, even when a sample is whole blood.

DISCLOSURE OF THE INVENTION

According to the present invention, there is provided a biosensor that is made of a single layer or plural layers of a porous material, having a reagent holding part and utilizing chromatography, in which a cell shrinkage reagent is carried on at least part of the reagent holding part, or at least part of a chromatographically developed part which is upstream of the reagent holding part.

According to the biosensor that is constituted as described above, cell components in an added liquid specimen shrink by contact with the cell shrinkage reagent, and the cell components can penetrate a chromatographic carrier efficiently and sufficiently without adding a development solution, whereby the quantity of liquid flowing chromatographically downstream is increased. Therefore, even when whole blood or a bacteria solution is a sample, a high-accuracy analysis can be performed easily and quickly with less cost. The cell shrinkage described here refers to a state where the cell shrinks by the action of osmotic pressure of the cell under a condition in which a substance that can pass through the cell membrane is in high concentration, utilizing the property of membrane equilibrium of the cell. It is favorable that the cell shrinkage reagent is a substance having the effect of making the cell shrink by the action of osmotic pressure.

According to the present invention, in the biosensor, a liquid specimen to be added is whole blood.

According to the biosensor that is constituted as described above, there is no need for an operation of previously eliminating hemocyte components in the whole blood, whereby a high-accuracy blood component analysis can be performed easily and quickly, with less cost.

According to the present invention, in the biosensor, a liquid specimen to be added is a solution including bacteria.

According to the biosensor that is constituted as described above, there is no need for an operation of previously eliminating or crushing cell components in the bacteria solution, where a high-accuracy analysis can be performed easily and quickly, with less costs.

According to the present invention in the biosensor, the cell shrinkage reagent is inorganic salt.

According to the biosensor that is constituted as described above, the cell components in an added liquid specimen shrink by contact with the inorganic salt, whereby the cell components can penetrate a chromatographic carrier efficiently and sufficiently without adding a development solution. Accordingly, the quantity of the liquid flowing chromatographically downstream is increased, whereby even when whole blood or a bacteria solution is a sample, a high-accuracy analysis can be performed easily and quickly, with less cost.

According to the present invention, in the biosensor, the cell shrinkage reagent is amino acid.

According to the biosensor that is constituted as described above, cell components in an added liquid specimen shrink by contact with amino acid, and the cell components can penetrate the chromatographic carrier efficiently and sufficiently without adding a development solution, whereby the quantity of the liquid flowing chromatographically downstream is increased. Therefore, even when whole blood or a bacteria solution is a sample, a high-accuracy analysis can be performed easily and quickly, with less cost.

According to the present invention, in the biosensor, the cell shrinkage reagent is saccharide.

According to the biosensor that is constituted as described above, cell components in an added liquid specimen shrink by contact with saccharide, and can penetrate the chromatographic carrier efficiently and sufficiently without adding a development solution, whereby the quantity of the liquid flowing chromatographically downstream is increased. Therefore, even when whole blood or a bacteria solution is a sample, a high-accuracy analysis can be performed easily and quickly with less cost.

According to the present invention, in the biosensor, a carrier that carries the cell shrinkage reagent is dried naturally or dried by air-drying.

According to the biosensor that is constituted as described above, denaturation of the cell shrinkage reagent and the like is reduced, whereby the cell components can shrink efficiently.

According to the present invention, in the biosensor, a carrier that carries the cell shrinkage reagent is dried by freeze-drying.

According to the biosensor that is constituted as described above, the crystals of the cell shrinkage reagent are fine grained and easily dissolved, whereby the cell components can shrink in a shorter time.

According to the present invention, in the biosensor, a carrier that carries the cell shrinkage reagent is dried by heat drying.

According to the biosensor that is constituted as described above, the cell shrinkage reagent can be dried in a shorter time, thereby simplifying manufacturing steps.

According to the present invention, in the biosensor, the biosensor is a one-step immunochromatographic test strip.

According to the biosensor that is constituted as described above, there is no need to previously preprocess a liquid specimen including cell components such as whole blood, and measurement targets in wide fields can be measured by obtaining an antibody or an antigen for the measurement target, utilizing an immuno reaction. Therefore, in cases where the liquid specimen including cell components such as whole blood is employed, easy and quick measurement can be performed. Here, one step refers to an operation which, in its measurement operation, does not require preprocessing of the liquid specimen including cell components such as the whole blood, and only requires spotting and sticking of the liquid specimen to a test strip but does not require the need to use a development solution that is different from the liquid specimen for the test strip before and after spotting and sticking of the liquid specimen or to carry out a washing operation for the purpose of B/F separation. The immunochromatographic test strip refers to a sensor for detecting a target substance in the liquid specimen utilizing the antigen-antibody reaction, on the carrier on which chromatographic development is performed.

According to the present invention, in the biosensor, the biosensor is a dry analytical element.

According to the biosensor that is constituted as described above, the entire biosensor is a dry carrier, so that it is not only easily portable but also there is no need for strict preservation environments or preservation conditions, whereby the biosensor that can be easily handled and preserved for a long time under all conditions can be obtained. The dry analytical element described here refers to one in which all members constituting the biosensor and a carried reagent are in dry states.

According to the present invention, there is provided a blood component analytical method in which a biosensor that is made of a single layer or plural layers of a porous material, having a reagent holding part and utilizing chromatography is employed, in which cell components shrink and the shrunk cell components are separated, in an area of at least part of the reagent holding part, or at least part of a chromatographically developed part that is upstream of the reagent holding part, on which a cell shrinkage reagent is carried.

According to the blood component analytical method that is constructed as described above, penetration can be obtained sufficiently without adding a development solution, and the quantity of the liquid flowing chromatographically downstream is increased. Therefore, even when whole blood is a sample, a high-accuracy blood component analysis can be performed easily and quickly with less cost.

According to the present invention, in the blood component analytical method, a blood specimen to be added is whole blood.

According to the blood component analytical method that is constructed as described above, there is no need for an operation of previously eliminating hemocyte components in the whole blood, whereby a high-accuracy blood component analysis can be performed easily and quickly with less cost.

According to the present invention, in the blood component analytical method, the cell shrinkage reagent is inorganic salt.

According to the blood component analytical method that is constituted as described above, penetration can be obtained sufficiently without adding a development solution, and the quantity of the liquid flowing chromatographically downstream is increased. Therefore, even when whole blood is a sample, a high-accuracy blood component analysis can be performed easily and quickly with less cost.

According to the present invention, in the blood component analytical method, the cell shrinkage reagent is amino acid.

According to the blood component analytical method that is constituted as described above, penetration can be obtained sufficiently without adding a development solution, and the quantity of the liquid flowing chromatographically downstream is increased. Therefore, even when whole blood is a sample, a high-accuracy blood component analysis can be performed easily and quickly with less cost.

According to the present invention, in the blood component analytical method, the cell shrinkage reagent is saccharide.

According to the blood component analytical method that is constructed as described above, penetration can be obtained sufficiently without adding a development solution, and the quantity of the liquid flowing chromatographically downstream is increased. Therefore, even when whole blood is used as a sample, a high-accuracy blood component analysis can be performed easily and quickly with less cost.

According to the present invention, in the blood component analytical method, a carrier that carries the cell shrinkage reagent is dried naturally or dried by air-drying.

According to the blood component analytical method that is constructed as described above, a carrier that carries the cell shrinkage reagent can be dried in a stable state, whereby denaturation of the cell shrinkage reagent being dried and the like can be suppressed.

According to the present invention, in the blood component analytical method, a carrier that carries the cell shrinkage reagent is dried by freeze-drying.

According to the blood component analytical method that is constructed as described above, the crystals of the cell shrinkage reagent are fine grained and easily dissolved, whereby the cell components can shrink in a shorter time.

According to the present invention, in the blood component analytical method, a carrier that carries the cell shrinkage reagent is dried by heat drying.

According to the blood component analytical method that is constructed as described above, the drying time of the carrier that carries the cell shrinkage reagent is reduced, and the cell shrinkage reagent can be dried in a shorter time, thereby simplifying manufacturing steps.

According to the present invention, in the blood component analytical method, the concentration of the cell shrinkage reagent is 0.05-0.3M.

According to the blood component analytical method that is constructed as described above, the cell components can shrink to optimal sizes, and consequently the cell component separation efficiency is increased.

According to the present invention, in the blood component analytical method, the biosensor is a one-step immunochromatographic test strip.

According to the blood component analytical method that is constructed as described above, there is no need to previously carry out preprocessing such as centrifugation to eliminate cell components in whole blood, and measurement targets in wide fields can be measured by obtaining an antigen or an antibody for the measurement target, utilizing an immuno reaction. Therefore, even when whole blood is employed, easy and quick measurement can be performed with a very small quantity of blood.

According to the present invention, in the blood component analytical method, the biosensor is a dry analytical element.

According to the blood component analytical method that is constructed as described above, the entire biosensor is a dry carrier, so that it is not only easily portable but also there is no need for strict preservation environments or preservation conditions, whereby a blood component analytical method that is easily handled can be obtained.

According to the present invention, there is provided a blood component analytical method in which a biosensor that is made of a single layer or plural layers of a porous material, having a reagent holding part and utilizing chromatography is employed, in which cell components shrink and chromatographically developed in a state where shrunk cell components are mixed, in an area of at least part of the reagent holding part, or at least part of a chromatographically developed part that is upstream of the reagent holding part, on which a cell shrinkage reagent is carried.

According to the blood component analytical method that is constructed as described above, penetration can be obtained on a chromatographic carrier efficiently without causing clogging and sufficiently without addition of a development solution, whereby the quantity of the liquid flowing chromatographically downstream is increased. Therefore, even when whole blood is used as a sample, a high-accuracy blood component analysis is performed easily and quickly with less cost.

According to the present invention, in the blood component analytical method, a blood specimen to be added is whole blood.

According to the blood component analytical method that is constructed as described above, there is no need to previously perform an operation of eliminating hemocyte-components in the whole blood, whereby a high-accuracy blood component analysis can be performed easily and quickly, with less cost.

According to the present invention, in the blood component analytical method, the cell shrinkage reagent is inorganic salt.

According to the blood component analytical method that is constructed as described above, penetration can be obtained on a chromatographic carrier efficiently without causing clogging and sufficiently without addition of a development solution, and the quantity of the liquid flowing the chromatographically downstream is increased. Therefore, even when whole blood is a sample, a high-accuracy blood component analysis can be performed easily and quickly with less cost.

According to the present invention, in the blood component analytical method, the cell shrinkage reagent is amino acid.

According to the blood component analytical method that is constructed as described above, penetration can be obtained on a chromatographic carrier efficiently without causing clogging and sufficiently without addition of a development solution, whereby the quantity of the liquid flowing the chromatographically downstream is increased. Therefore, even when whole blood is used as a sample, a high-accuracy blood component analysis can be performed easily and quickly, with less cost.

According to the present invention, in the blood component analytical method, the cell shrinkage reagent is saccharide.

According to the blood component analytical method that is constructed as described above, penetration can be obtained on a chromatographic carrier efficiently without causing clogging, and sufficiently without adding a development solution, whereby the quantity of the liquid flowing chromatographically downstream is increased. Therefore, even when whole blood is employed as a sample, a high-accuracy blood component analysis can be performed easily and quickly, with less cost.

According to the present invention, in the blood component analytical method, a carrier that carries the cell shrinkage reagent is dried naturally or dried by air-drying.

According to the blood component analytical method that is constructed as described above, a carrier that carries the cell shrinkage reagent can be dried in a stable state, whereby denaturation and the like of the cell shrinkage reagent being dried can be suppressed.

According to the present invention, in the blood component analytical method, a carrier that carries the cell shrinkage reagent is dried by freeze-drying.

According to the blood component analytical method that is constructed as described above, the crystals of the cell shrinkage reagent are fine grained and easily dissolved, whereby the cell components can shrink in a shorter time.

According to the present invention, in the blood component analytical method, a carrier that carries the cell shrinkage reagent is dried by heat drying.

According to the blood component analytical method that is constructed as described above, the drying time of the carrier that carries the cell shrinkage reagent is reduced, whereby denaturation and the like of the cell shrinkage reagent being dried can be suppressed.

According to the present invention, in the blood component analytical method, the concentration of the cell shrinkage reagent is 0.1-5.0M.

According to the blood component analytical method that is constructed as described above, the cell component can shrink to optimal sizes, and consequently the whole blood can be made penetrate the carrier without causing clogging.

According to the present invention, in the blood component analytical method, the biosensor is a one-step immunochromatographic test strip.

According to the blood component analytical method that is constructed as described above, there is no need to previously carry out preprocessing such as centrifugation to eliminate cell components in whole blood, and measurement targets in wide fields can be measured by obtaining an antigen or an antibody for the measurement target, utilizing an immuno reaction. Therefore, a blood component analytical method can be obtained in which, in cases where a liquid sample including cell components such as whole blood is employed, an easy and quick measurement can be performed.

According to the present invention, in the blood component analytical method, the biosensor is a dry analytical element.

According to the blood component analytical method that is constructed as described above, the entire biosensor is a dry carrier, so that it is not only easily portable but also there is no need for strict preservation environments or preservation conditions, whereby a blood component analytical method that is easily handled can be obtained.

BEST MODE FOR CARRYING OUT THE INVENTION

Hereinafter, embodiments of the present invention will be described with reference to the drawings. The embodiments described here are only examples and the present invention is not limited to these embodiments.

Embodiment 1

Figure 1:
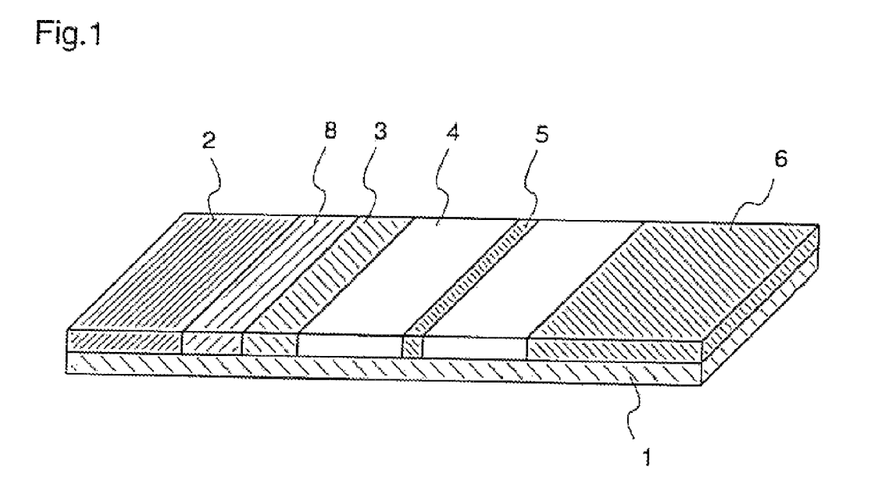
FIG. 1 is a diagram illustrating a lateral flow-type biosensor utilizing chromatography according to a first embodiment of the present invention.

FIG. 1 is a diagram illustrating a lateral flow-type biosensor utilizing chromatography according to a first embodiment.

As shown in FIG. 1, the biosensor according to the first embodiment includes a carrier support 1 that is made of plastic or the like, and a specimen addition part 2 that is constituted by fabric or glass fiber filter paper having a high water absorbing property, to which part a liquid specimen is added or applied, a shrinkage reagent holding part 8 where a cell shrinkage reagent having an ability of contracting cell components is solubly held on the fabric or the glass fiber filter paper, a marker reagent holding part 3 in which a marker reagent which produces some reaction with an analysis target is solubly held on the fabric or the glass fiber filter paper, a reaction layer 4 that is made of nitrocellulose or the like, a specific protein immobilization part 5 in which a specific protein is immobilized on an area of the reaction layer 4, and a water absorbing part 6 which finally absorbs the liquid specimen, which are formed on the carrier support 1.

The cell shrinkage reagent held by the shrinkage reagent holding part 8 is for example inorganic salt, amino acid, or saccharide. Here, the inorganic salt refers to inorganic compounds including salt, such as sodium chloride, potassium chloride, and sodium phosphate. The amino acid refers to compounds having the carboxyl group and the amino group in the same molecule, such as glycin and glutamic acid, and includes also imino acid such as proline and hydroxylprolin. The saccharide refers to sugar such as glucose, sucrose and trehalose, or sugar alcohol such as glucitol.

The reaction between the analysis target and the marker reagent refers to a specific bonding reaction between a ligand and a receptor such as an antigen-antibody reaction, or an arbitrary specific reaction such as an enzyme reaction.

The marker reagent held by the marker reagent holding part 3 refers to metallic sols such as gold colloid, nonmetallic sols, dye sols, colored particles, coloring matters, enzymes, proteins or the like.

Next, a blood component analytical method using the biosensor according to the first embodiment will be described.

Initially, a liquid specimen including cell components, such as whole blood and bacteria solution, is added to the specimen addition part 2. When the added liquid specimen reaches the shrinkage reagent holding part 8, the shrinkage reagent held by the shrinkage reagent holding part 8 is dissolved by the penetration of the liquid specimen, thereby contracting (shrinking) the cell components. Accordingly, the liquid specimen penetrates (permeates) chromatographically downstream without causing clogging, even under a state where the cell components are mixed.

Next, when the liquid specimen in which the contracted (shrunk) cell components are mixed reaches the marker reagent holding part 3, the marker reagent held on the marker reagent holding part 3 is dissolved by the penetration of the liquid specimen and then penetrates the reaction layer 4.

Then, in the specific protein immobilization part 5 on an area of the reaction layer 4, a reaction is produced with the marker reagent eluted from the marker reagent holding part 3. At this time, when the liquid specimen includes the analysis target, some color reaction is seen in the specific protein immobilization part 5.

Finally, the liquid specimen is absorbed by the water absorbing part 6, thereby completing the reaction.

As described above, according to the biosensor and the blood component analytical method of the first embodiment, the cell shrinkage reagent held on the shrinkage reagent holding part makes the cell components in the liquid specimen shrink. Therefore, even in situations where the cell components are mixed, the liquid specimen penetrates chromatographically downstream without causing clogging. Accordingly, even when whole blood or bacteria solution is the sample, it can be developed without previous preprocessing of the sample. Therefore, the development solution is not required to develop the sample solution chromatographically downstream, whereby the high-accuracy blood component analysis can be performed easily and quickly with reduced costs.

In the biosensor of the first embodiment, the specimen addition part can be omitted and the specimen can be directly added to the reaction layer.

Figure 2:
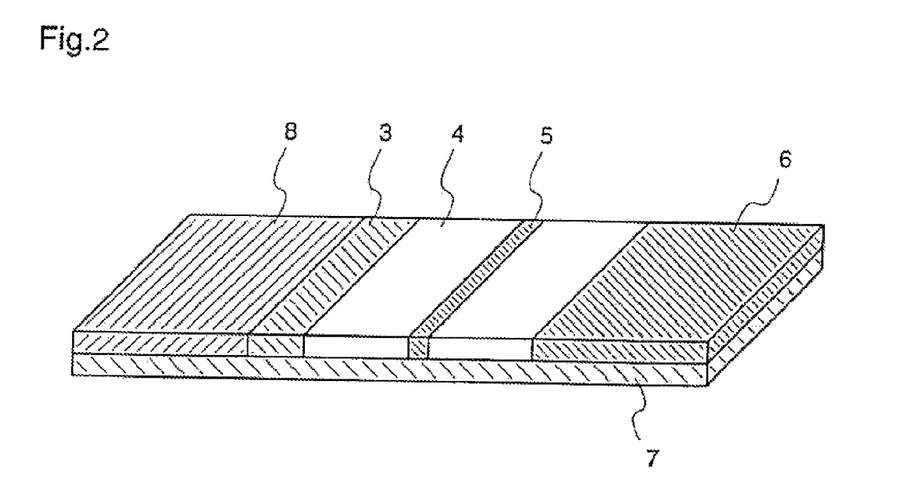
FIG. 2 is a diagram illustrating the lateral flow-type biosensor according to the first embodiment of the present invention, with a specimen addition part being omitted and a shrinkage reagent holding part serving also as a specimen addition part.

FIG. 2 is a diagram illustrating the lateral flow-type biosensor of the first embodiment, with the specimen addition part being omitted and the shrinkage reagent holding part serving also as a specimen addition part.

When the shrinkage reagent holding part serves also as the specimen addition part as shown in FIG. 2, the number of members and the number of steps can be reduced.

While the biosensor of the first embodiment is constituted by plural members, the biosensor can be constituted by a single-layer member that has a shrinkage reagent holding area on which the shrinkage reagent is solubly held, a marker reagent holding area on which the marker reagent is solubly held, and a specific protein immobilization part on which the specific protein is immobilized, all of which are formed on a reaction layer that is made of a porous material such as nitrocellulose.

Further, the biosensor of the present invention may be a dry analytical element. The dry analytical element described here refers to one in which all members constituting the biosensor and a carried reagent are in dry states. When the test strip is in a dry state, the entire biosensor is a dry carrier, so it is not only easily portable, but also strict preservation environments or preservation conditions are not required, whereby it can be easily handled and the long preservation under all conditions is enabled.

Further, the biosensor of the present invention may have a one-step immunochromatographic test strip. Here, the one-step refers to operations, in its measurement operation, requiring no preprocessing of a liquid specimen including cell components such as whole blood, and requiring only spotting and sticking of the liquid specimen onto a test strip, without the need to use a development solution that is different from the liquid specimen on the test strip before and after the spotting and sticking of the liquid specimen or the need for washing operation. The immunochromatographic test strip refers to a sensor for detecting a substance to be tested in the liquid specimen utilizing an antigen-antibody reaction on a carrier which is chromatographically developed. When the test strip is a one-step immunochromatographic test strip as described above, the need to previously carry out preprocessing of the liquid specimen including cell components such as whole blood is not required, and a measurement target in wide fields can be measured by obtaining an antigen or an antibody for the measurement target, using the immune reaction. Therefore, in cases where the liquid specimen including cell components such as whole blood is used, a simple and quick measurement is enabled.

Embodiment 2

Figure 3:
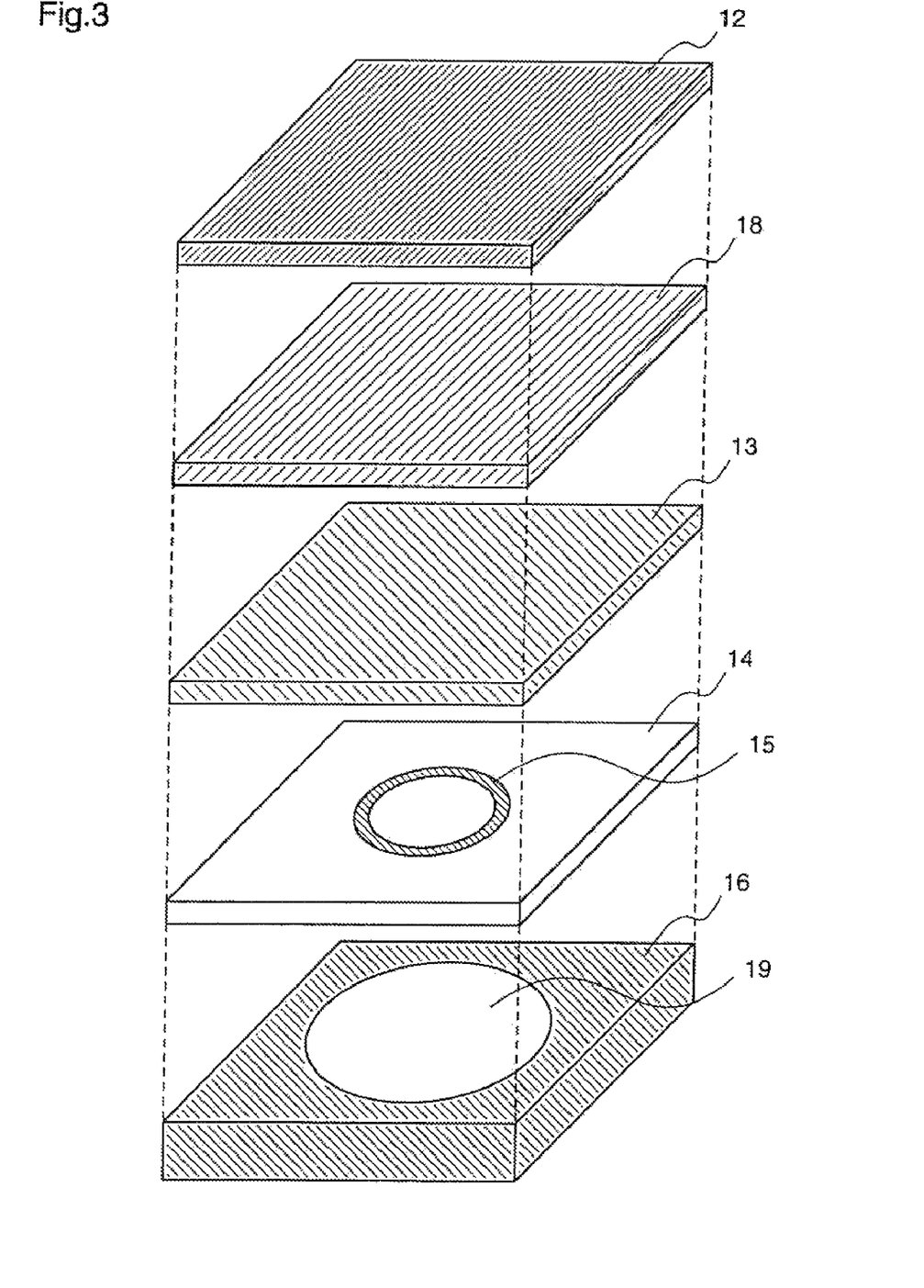
FIG. 3 is an exploded perspective view illustrating a flow through-type biosensor utilizing chromatography according to a second embodiment of the present invention.

FIG. 3 is an exploded perspective view illustrating a flow through-type biosensor employing chromatography according to a second embodiment of the present invention.

As shown in FIG. 3, the biosensor of the second embodiment includes a specimen addition part 12 that is made of fabric or glass fiber filter paper having a high water absorbing property, to which a liquid specimen is added or applied, a shrinkage reagent holding part 18 on which a cell shrinkage reagent having the ability to making cell components shrink is solubly held by the fabric or the glass fiber filter paper, a marker reagent holding part 13 on which a marker reagent that produces some reaction with an analysis target is solubly held by fabric or glass fiber filter paper, a reaction layer 14 that is made of nitrocellulose or the like, a specific protein immobilization part 15 on which a specific protein is immobilized in an area of the reaction layer 14, a water absorbing part 16 which finally absorbs the liquid specimen, and a result check window 19 for observing a result on the reaction layer 14, all of which are laminated one another.

The cell shrinkage reagent held by the shrinkage reagent holding part 18 is for example inorganic salt, amino acid, or saccharide. Here, the inorganic salt refers to inorganic compounds including salt, such as sodium chloride, potassium chloride, and sodium phosphate. The amino acid refers to compounds having the carboxyl group and the amino group in the same molecule such as glycin and glutamic acid, and also includes imino acid such as proline and hydroxylprolin. Further, the saccharide refers to sugar such as glucose, sucrose and trehalose, and sugar alcohol such as glucitol.

The reaction between the analysis target and the marker reagent refers to a specific bonding reaction between a ligand and a receptor such as an antigen-antibody reaction, or an arbitrary specific reaction such as an enzyme reaction.

The marker reagent held by the marker reagent holding part 13 refers to metallic sols such as gold colloid, nonmetallic sols, dye sols, colored particles, coloring matters, enzymes, proteins or the like.

Figure 4:
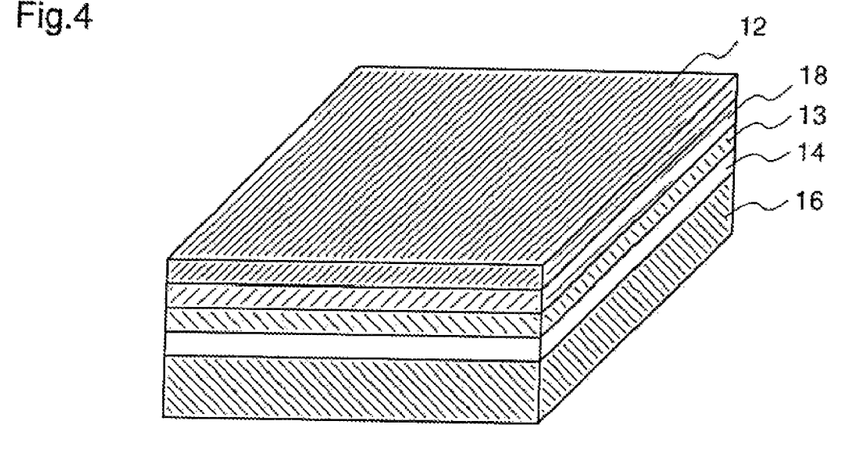
FIG. 4 is a perspective view illustrating the flow through-type biosensor according to the second embodiment of the present invention, seen from the side of a specimen addition part.
Figure 5:
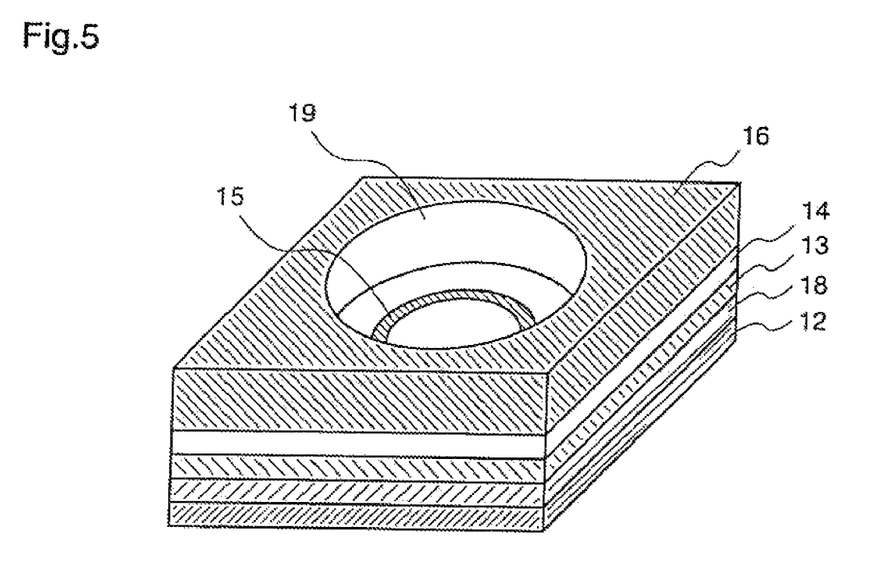
FIG. 5 is a perspective view illustrating the flow through-type biosensor according to the second embodiment of the present invention, seen from the side of a water absorbing part.

FIG. 4 is a perspective view illustrating the flow through-type biosensor of the second embodiment, seen from the side of the specimen addition part. FIG. 5 is a perspective view illustrating the flow through-type biosensor of the second embodiment, seen from the side of the water absorbing part.

Next, a blood component analytical method using the biosensor of the second embodiment will be described.

Initially, a liquid specimen including cell components such as whole blood and a bacteria solution is added to the specimen addition part 12. When this added liquid specimen reaches the shrinkage reagent holding part 18, the shrinkage reagent held by the shrinkage reagent holding part 18 is dissolved by penetration of the liquid specimen, thereby making the cell components shrink.

Next, when the liquid specimen in which the shrunk cell components are mixed reaches the marker reagent holding part 13, the marker reagent held by the marker reagent holding part 13 is dissolved by penetration of the liquid specimen, then the shrunk cell components are caught in the fiber of the fabric or glass fiber filter paper in the marker reagent holding part 13 and then separated. Accordingly, the liquid components penetrate the reaction layer 14 quickly.

Then, a reaction with the marker reagent eluted from the marker reagent holding part 13 is produced in the specific protein immobilization part 15 on an area of the reaction layer 14. At this time, when the analysis target is included in the liquid specimen, some color reaction is seen in the specific protein immobilization part 15.

Finally, the liquid specimen is absorbed by the water absorbing part 16, thereby completing the reaction.

As described above, according to the biosensor and the blood component analytical method of the second embodiment, the cell shrinkage reagent held by the shrinkage reagent holding part makes the cell components in the liquid specimen shrink. Therefore, the cell components caught in the fiber of the members laminated in the lower section, and separated, whereby the liquid components in the liquid specimen penetrate the reaction layer quickly. Accordingly, even when the whole blood or the bacteria solution is a sample, the high-accuracy blood component analysis can be performed with reduced costs and easily and quickly.

Here, in the biosensor of the second embodiment, its specimen addition part can be omitted and the specimen can be added directly to the reaction layer.

Figure 6:
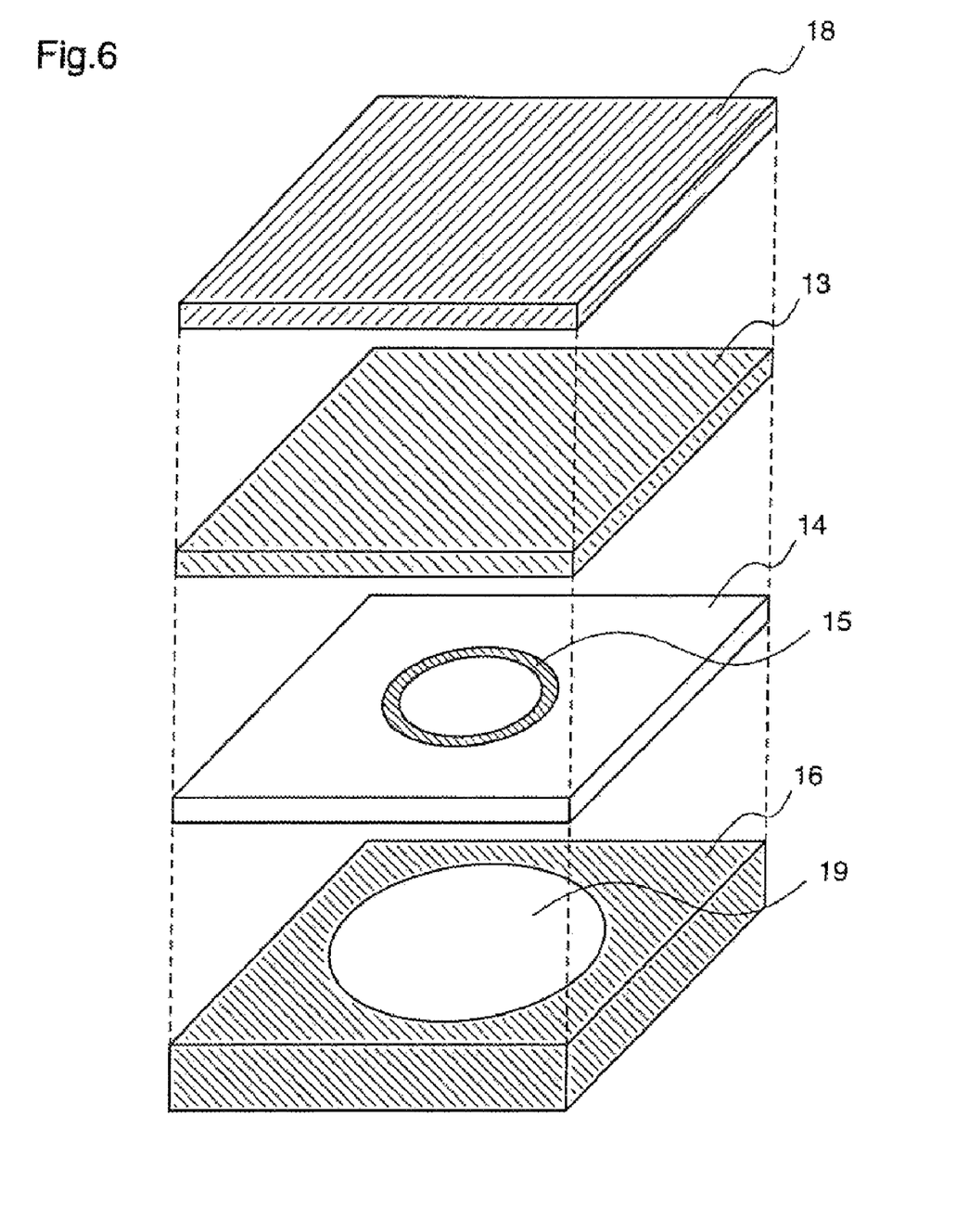
FIG. 6 is a perspective view illustrating the flow through-type biosensor according to the second embodiment of the present invention, with a specimen addition part being omitted and a shrinkage reagent holding part serving also as a specimen addition part.
Figure 7:
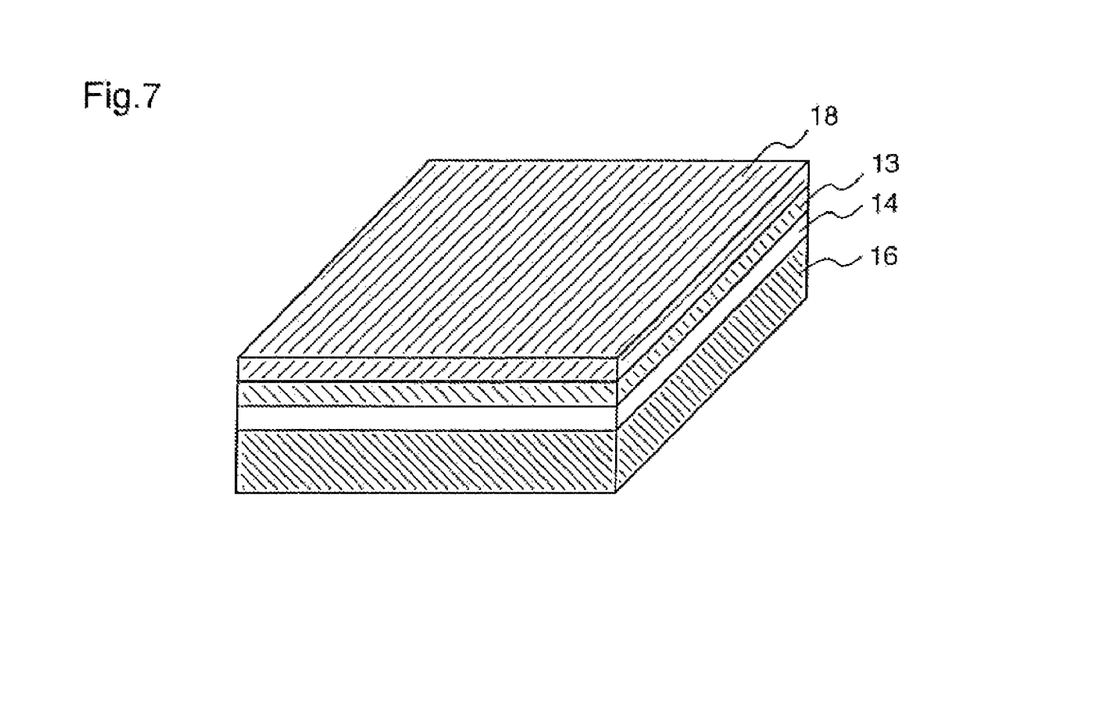
FIG. 7 is a perspective view illustrating the flow through-type biosensor according to the second embodiment of the present invention, with the specimen addition part being omitted and the shrinkage reagent holding part serving also as a specimen addition part, seen from the side of the shrinkage reagent holding part.
Figure 8:
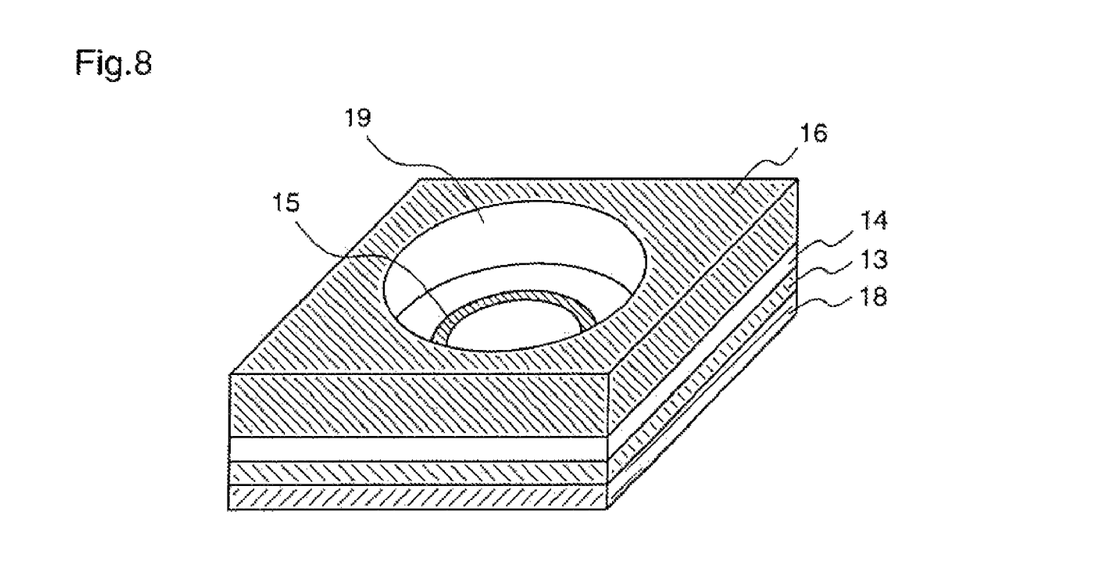
FIG. 8 is a perspective view illustrating the flow through-type biosensor according to the second embodiment of the present invention, with a specimen addition part being omitted and the shrinkage reagent holding part serving also as a specimen addition part, seen from the side of a water absorbing part.

FIG. 6 is a perspective view illustrating the flow through-type biosensor of the second embodiment, with the specimen addition part being omitted and the shrinkage reagent holding part serving as also a specimen addition part. FIG. 7 is a perspective view illustrating the flow through-type biosensor of the second embodiment, with the specimen addition part being omitted and the shrinkage reagent holding part serving also as the specimen addition part, seen from the side of the shrinkage reagent holding part. FIG. 8 is a perspective view illustrating the flow through-type biosensor of the second embodiment, with the specimen addition part being omitted and the shrinkage reagent holding part serving also as the specimen addition part, seen from the side of the water absorbing part.

When the shrinkage reagent holding part serves also as the specimen addition part as shown in FIGS. 6 to 8, the number of members and the number of steps can be reduced.

Further, for the biosensor according to the first or second embodiment, the chromatography material that is constituted by an arbitrary porous carrier such as nitrocellulose, fabric, and glass fiber filter paper is used. Generally, the biosensor that is made of such material has the capability of analyzing and detecting a specific substance using a measurement principle owing to an arbitrary specific reaction such as an antigen-antibody reaction, and qualitatively or quantitatively analyzing the substance. In the first and second embodiment the description has been given taking an antigen-antibody reaction using a marker as an example, but any thing such as enzymes may be used as long as some changes occur before and after the reaction.

Further, the biosensor of the present invention may be a dry analytical element. Here, the dry analytical element described here refers to one in which all members constituting a biosensor and a carried reagent are in dry states. When a test strip is in a dry state, the biosensor is a dry carrier as a whole, so that not only it is easily portable, but also there is no need for strict preservation environments or preservation conditions. Accordingly, this can be easily handled, and long-term preservation under all conditions can be performed.

The biosensor according to the present invention may have a one-step immunochromatographic test strip. Here, the one step refers to an operation which, in its measurement operation, requires only spotting and sticking of a liquid specimen onto a test strip but does not require the need for preprocessing of the liquid specimen including cell components such as whole blood, and does not need to use a development solution that is different from the liquid specimen for the test strip before and after the spotting and sticking of the liquid specimen or to perform a washing operation. The immunochromatographic test strip refers to a sensor that detects a target substance in the liquid specimen utilizing an antigen-antibody reaction on a carrier on which chromatographic development is performed. When a one-step immunochromatographic test strip is employed, there is no need to previously perform preprocessing of the liquid specimen including cell components such as whole blood, and thus measurement targets in wide fields can be measured by obtaining an antigen or an antibody for the measurement targets, with utilizing the immuno reaction. Therefore, in cases where the liquid specimen including cell components such as whole blood is used, the simple and quick measurement is enabled.

EXAMPLES

The method for implementing the present invention will be described in more detail, with reference to following examples. Here, the present invention is not limited to the following examples.

Example 1

Qualitative Analysis of hCG in Whole Blood by Lateral Flow-Type Biosensor Utilizing Chromatography An immuno biosensor including an anti hCG-(antibody immobilized line, and a wide band of a complex of an anti hCG-a antibody and a gold colloid in a nitrocellulose membrane was manufactured. This biosensor is a lateral flow-type biosensor having a configuration as shown in FIG. 1 and was manufactured as follows:

a) Preparation of Biosensor

An anti hCG-β antibody solution which was diluted by a phosphate buffered solution to regulate its concentration was prepared. This antibody solution was applied onto a nitrocellulose membrane using a solution discharge device. Thereby, a detecting antibody immobilized line was obtained on the nitrocellulose membrane. After dried, this nitrocellulose membrane was immersed into a Tris-HCl buffer solution containing 1-% skim milk, and shaken gently. Then, 30 minutes later, the membrane was moved into a Tris-HCl buffer solution tank, and shaken gently for 10 minutes. Thereafter, the membrane was shaken gently in another Tris-HCl buffer solution tank for another 10 minutes, thereby washing the membrane. After the twice washing, the membrane was picked up from the liquid tank and dried at room temperature.

The gold colloid was prepared by adding a 1-% citric acid solution to a circulating 100° C. solution of 0.01% chloroauric acid. After the circulation was continued for 30 minutes, the gold colloid was set aside at room temperature to be cooled. An anti hCG-α antibody was added to the gold colloid which had been adjusted to pH9 with a 0.2M potassium carbonate solution and then agitated for several minutes. Thereafter, a quantity of 10% BSA (bovine serum albumin) solution of pH9 was added so as to finally obtain a 1% solution, and then agitated, whereby an antibody-gold colloid complex (marker antibody) was prepared. The marker antibody solution was centrifuged at 4° C. and 20000 G for 50 minutes, thereby isolating the marker antibody. Then the isolated marker antibody was suspended into a washing buffer (1% BSA-phosphate buffer) and thereafter centrifuged, thereby washing and isolating the marker antibody. This marker antibody was suspended by a washing buffer, filtered by a 0.8-μm filter, then regulated to reduce the quantity to one tenth the quantity of the initial gold colloid solution, and an obtained solution was stored at 4° C.

The marker antibody solution was set in the solution discharge device, applied to a position which is at a distance from the antibody immobilized position on the anti hCG-β antibody immobilized dry membrane, and then the membrane was dried. Thereby, a marker reagent holding part was obtained on the immobilized membrane.

A potassium chloride aqueous solution that was adjusted to 0.15M was spotted and stuck to fabric, by 0.1 ml per a unit area, then immediately frozen by liquid nitrogen, thereby performing freeze-drying. Thus, a shrinkage reagent holding member that was impregnated with potassium chloride was obtained.

The antibody immobilized membrane including the marker reagent holding part that was prepared as described above was affixed on the carrier support, then the shrinkage reagent holding member, fabric as the specimen addition part, and glass fiber filter paper as the water absorbing part were added thereto, thereafter cut into small pieces of 0.5-cm width, thereby preparing the biosensor.

b) Preparation of Specimen

Human blood to which heparin was added as an anticoagulant was adjusted to have a hematocrit value of 45%. Then, hCG solutions of known concentrations of were added to this blood, whereby hCG solutions of various known concentrations were prepared.

c) Measurement of Coloration Degree on Biosensor

Whole blood including hCG was added to the specimen addition part on the biosensor by about 150 μm, developed in the direction of the water absorbing part, and made cause an antigen-antibody reaction, thereby producing a color reaction in the antibody immobilized part. Then the coloration state five minutes after the specimen addition to the biosensor was checked visually. Further, the time which it took the blood to penetrate the reaction layer by 2 cm on the biosensor to the chromatographically downstream side was measured.

Figure 9:
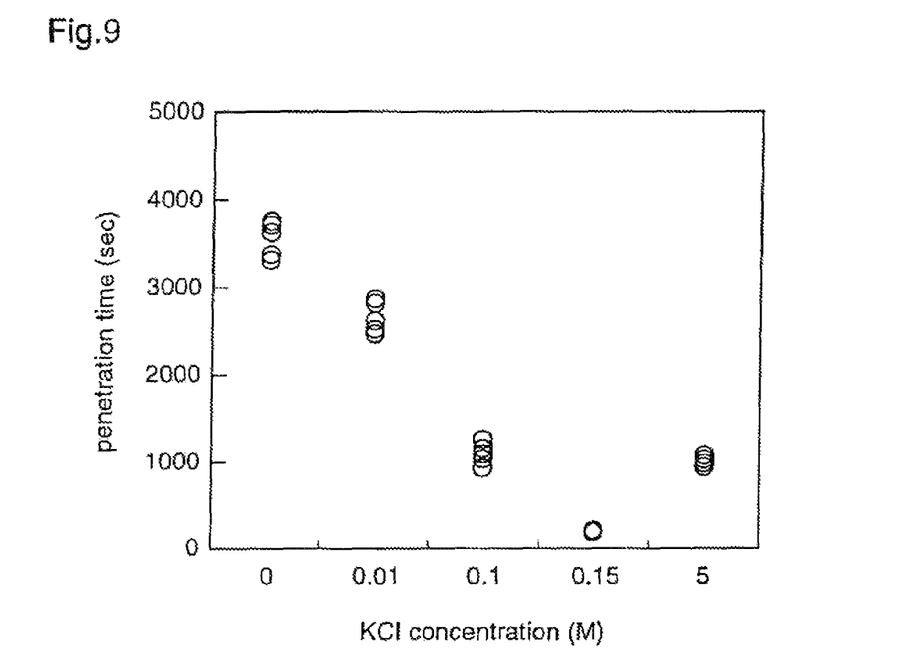
FIG. 9 is a diagram showing the rates of solution penetration onto a reaction layer of the lateral flow-type biosensor according to the first embodiment of the present invention with changes in the concentration of a shrinkage reagent.

FIG. 9 is a diagram showing the rates of solution penetration onto the reaction layer with changes in the concentration of the shrinkage reagent in the lateral flow-type biosensor according to the first example. More specifically, this figure shows the time which it takes the blood to penetrate the reaction layer by 2 cm when the KCl concentration is changed to 0.01M, 0.1M, 0.15M or 5M, the shrinkage reagent holding part 3 carrying the KCl solution of each concentration is incorporated into the sensor, and then the blood having a 45% hematocrit value is added. Here, it can be seen that when no KCl is included, it takes about one hour to penetrate, while as the KCl concentration increases as 0.01M, 0.1M, and 0.15M, the penetration time is reduced more.

From the above-mentioned result, it is understood that the area that holds the cell shrinkage reagent, provided in the lateral flow-type biosensor according to this first example, is greatly related to the reduction in the penetration rate on the reaction layer.

Here, when the concentration of the cell shrinkage reagent is set at 0.1M-0.5M, the cell components can shrink to optimal sizes. Consequently, the whole blood can be made penetrate quickly without causing clogging on the carrier.

In this first example, the carrier that carries the cell shrinkage reagent (a potassium chloride aqueous solution in this first example) is dried by freeze-drying. Therefore, the crystals of the cell shrinkage reagent are fine grained and easily dissolved, whereby the cell components can shrink in a shorter time.

While in this first example the carrier which carries the cell shrinkage reagent is dried by freeze-drying, it may be dried naturally or dried by air-drying. Thereby, the denaturation of the cell shrinkage reagent and the like is reduced, whereby the cell components can shrink efficiently. Further, the carrier that carries the cell shrinkage reagent may be dried by heat drying. Thereby, the drying of the cell shrinkage reagent in a shorter time is enabled, thereby simplifying manufacturing processes.

Further, in the biosensor of the first example, the chromatography material that is constituted by an arbitrary porous carrier, such as nitrocellulose and glass fiber filter paper is employed, and, generally the biosensor that is constituted by such material has the capability of analyzing and detecting a specific substance using an arbitrary specific measurement principle such as an antigen-antibody reaction, and qualitatively or quantitatively analyzing the substance. In this first example, the case of an antigen-antibody reaction using the marker has been described while any thing such as enzymes may be used as long as some changes occur before and after the reaction.

Further, the test strip that is constituted by plural porous carriers including fabric as the specimen addition part and glass fiber filter paper as the water absorbing part has been described as an example. However, the test strip may have a single layer structure from which the fabric and the glass fiber filter paper is eliminated and which is provided with the antibody immobilized part which is immobilized on the porous carriers, the marker reagent holding part on which a marker reagent is elutably held, and the shrinkage reagent holding part on which a cell shrinkage reagent is elutably held.

Example 2

Qualitative Analysis of hCG in Whole Blood Employing Flow Through-Type Biosensor Utilizing Chromatography A biosensor which is constituted by a nitrocellulose membrane including an anti hCG-β antibody immobilized area, a marker reagent holding part including a marker that is constituted by a complex of an anti hCG-a antibody and a gold colloid, and a shrinkage reagent holding part including a hemocyte shrinkage reagent that makes the hemocyte shrink in the added blood was prepared. This biosensor is a flow through-type biosensor having a configuration as shown in FIG. 3. This biosensor was manufactured as follows.

a) Preparation of Biosensor

Glass fiber filter paper GA100 (Advantech Co., Ltd. made) was prepared as a specimen addition part.

As for the shrinkage reagent holding part, a NaCl aqueous solution was prepared, then 140 μl of this aqueous solution was spotted and stuck to the glass fiber filter paper GA100 (Advantech Co., Ltd. made), immediately frozen by liquid nitrogen, and thereafter freeze-dried. Thereby, the shrinkage reagent holding part was prepared.

The gold colloid was prepared by adding 1% citric acid solution to a circulating 100° C. solution of a 0.01% chloroauric acid. After the circulation was continued for 30 minutes, the solution was cooled. An anti hCG-a antibody was added to the gold colloid solution which was adjusted to pH9 by a 0.2M potassium carbonate solution, agitated for several minutes, and thereafter a 10% BSA (bovine serum albumin) solution of pH9 was added thereto to finally obtain a 1-% solution and agitated, thereby preparing an antibody-gold colloid complex (marker antibody). The marker antibody solution was centrifuged for 50 minutes at 4° C. and 20000 G, thereby isolating the marker antibody, then the isolated marker antibody was suspended in a washing buffer (1% BSA-phosphate buffer) and thereafter centrifuged, thereby washing and isolating the marker antibody. This marker antibody was suspended in a washing buffer, filtered by a 0.8-μm filter, then adjusted to reduce the quantity to one tenth of the quantity of the initial gold colloid solution, and the obtained solution was stored at 4° C.

This gold colloid solution was spotted and stuck by 140 μl to the glass fiber filter paper GA100 (Advantech Co., Ltd. made), immediately frozen by liquid-nitrogen, and then freeze-dried. Thereby, the marker reagent holding part was prepared.

An anti hCG-β antibody solution which was diluted by a phosphate buffered solution to adjust the concentration was prepared. This antibody solution was applied to a nitrocellulose membrane using a solution discharge device. Thereby, a detecting antibody immobilized area was obtained on the nitrocellulose membrane. After dried, this nitrocellulose membrane was immersed into a Tris-HCl buffer solution containing a 1% BSA-0.5% skimmed milk, and shaken gently for 30 minutes. Then 30 minutes later, the membrane was moved into a Tris-HCl buffer solution tank, shaken gently for 10 minutes, thereafter shaken gently for another 10 minutes in another Tris-HCl buffer solution tank, thereby performing washing of the membrane. After the twice washing, the membrane was picked up from the liquid tank and dried at room temperature, to obtain a reaction layer having a specific protein immobilized part.

As the water absorbing part, glass fiber filter paper GA200 (Advantech Co., Ltd. made) that is provided with a result check window was prepared so as to judge the result on the reaction layer.

The respective members which were prepared as described above were laminated as shown in FIG. 3 and covered by a case, thereby obtaining a biosensor.

b) Preparation of Specimen

Human blood to which heparin was added as an anticoagulant was adjusted to obtain a hematocrit value of 45%. Then, hCG solutions of known concentrations were added to this blood, whereby hCG solutions of various known concentrations were prepared.

c) Measurement

The blood including hCG was added by 200 μl to the specimen addition part of the analytical device which was assembled as described above, then developed in the lower direction of the laminated biosensor, and an antigen-antibody reaction was caused, thereby producing a color reaction in the antibody immobilized part. The state of coloration three minutes after the specimen addition to the biosensor was visually checked from the result check window located at the lower part of the biosensor. Further, the biosensor that finished the measurement was disassembled, and the state of hemocyte adhesion on the reaction layer was checked.

Figure 10:
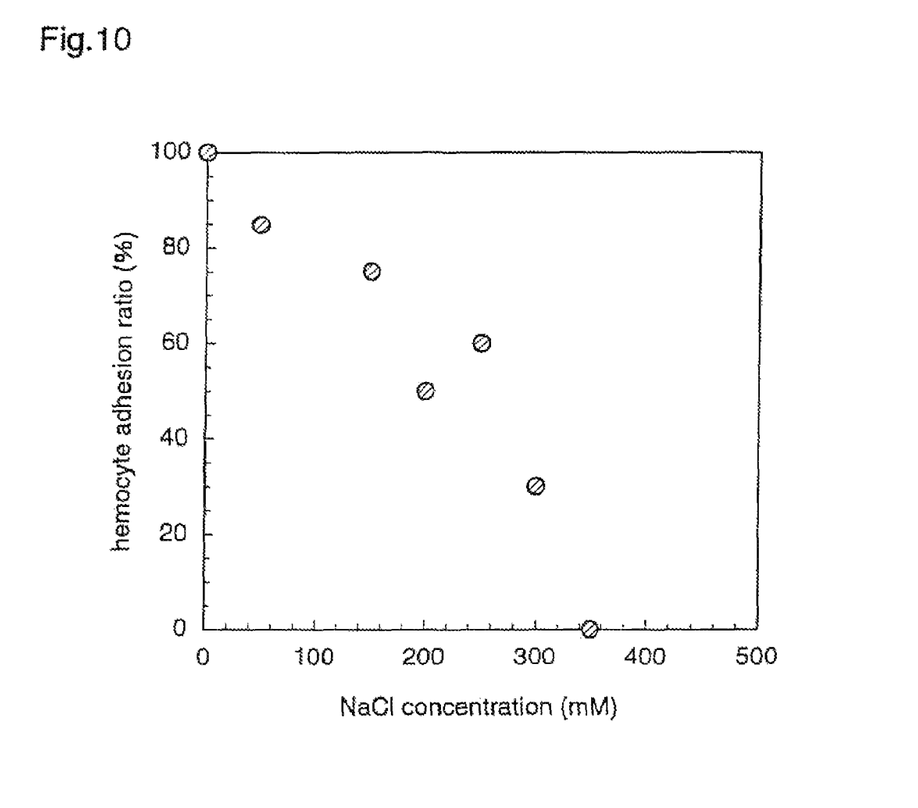
FIG. 10 is a diagram showing the ratios of hemocyte adhesion to a reaction layer of the flow through-type biosensor according to the second embodiment of the present invention with changes in the concentration of a shrinkage reagent.

FIG. 10 is a diagram showing the ratios of hemocyte adhesion onto the reaction layer with changes in the concentration of the shrinkage reagent in the flow through-type biosensor according to the second embodiment. To be more specific, this figure shows the possibility that hemocytes reach the reaction layer when the NaCl-concentration is changed to 5.0 mM, 150 mM, 200 mM, 250 mM, 300 mM, or 350 mM, a shrinkage reagent holding part which carries the NaCl solution of each concentration is incorporated into a sensor, and blood having a 45% hematocrit value is added thereto. It can be seen that in the case where no NaCl is included, the adhesion of the hemocytes to the reaction layer is observed by a ratio of 100%, while as the NaCl concentration increases from 50 mM, the ratio of hemocyte adhesion to the reaction layer decreases gradually and the hemocytes do not adhere at all in the case of 350 mM.

From the above-mentioned results, it is understood that the area holding the cell shrinkage reagent, provided in the lateral flow-type biosensor according to the second example, greatly contributes to the increases in the efficiency of separation of the cell components in the sample.

Here, when the concentration of the cell shrinkage reagent is set at 0.05M to 0.3M, the cell components can shrink to optimal sizes, and consequently the cell component separation efficiency can be increased.

In this second example, since the carrier that carries the cell shrinkage reagent (a sodium chloride aqueous solution in this second example) is dried by freeze-drying, the crystals of the cell shrinkage reagent are fine grained and easily dissolved, whereby the cell components can shrink in a shorter time.

In this second example, the carrier that carries the cell shrinkage reagent is dried by freeze-drying, while it may be dried naturally or dried by air-drying. Thereby, the denaturation of the cell shrinkage reagent and the like is reduced, and the cell components can shrink efficiently. Further, the carrier that carries the cell shrinkage reagent can be dried by heat drying. Thereby, the drying of the cell shrinkage reagent in a shorter time is enabled, thereby simplifying the manufacturing processes.

Further, in the biosensor of the second example, the gold colloid is employed as a marker, while it is also possible to mark an enzyme in an immobilized antibody and use a specimen that can produce a color reaction due to the enzyme reaction as a marker reagent.

In the biosensor of the second example, the chromatography material which is constituted by an arbitrary porous carrier, such as nitrocellulose and glass fiber filter paper is employed, and generally the biosensor that is made of such material has the capability of analyzing and detecting a specific substance using an arbitrary specific measurement principle such as the antigen-antibody reaction and qualitatively or quantitatively analyzing the substance. While in the second example the case where the antigen-antibody reaction using a marker has been described as an example, any thing like an enzyme may be used as long as some changes occur before and after the reaction.

INDUSTRIAL AVAILABILITY

According to the biosensor and the blood component analytical method of the present invention, even when whole blood is used as a sample, a high-accuracy blood component analysis can be carried out easily and quickly, with less expenses, and without the need to previously carrying out some processing for the blood or the need for a development solution for developing a sample solution, and the present invention is especially suitable for a one-step biosensor and blood component analytical method.

The invention claimed is:

1. A biosensor that is made of a single layer or plural layers of a porous material, said biosensor having a reagent holding part which holds a reagent for analyzing an analyte in a liquid specimen having cell components contained therein, said biosensor analyzing target components in the liquid specimen by utilizing chromatography, said biosensor further comprising:

a carrier carrying a cell shrinkage reagent having the ability of making the cell components of said liquid specimen shrink on at least a part of an area of said carrier, wherein the cell shrinkage reagent is saccharide, and wherein the shrunk cell components are made smaller by said cell shrinkage reagent, said area ranging from a specimen addition part to which the liquid specimen is added to a reagent holding part thereof; and a reaction layer chromatographically downstream of said carrier on which a reaction between the analyte in the liquid specimen and a reagent eluted from the reagent holding part is carried out, permitting analysis of the analyte in the liquid specimen, wherein the shrunk cell components of said liquid specimen permeate together with the liquid specimen into said reaction layer in a mixed state for analysis to occur.

* * * * *